(12) United States Patent
Atalar et al.

(10) Patent No.: US 10,641,847 B2
(45) Date of Patent: May 5, 2020

(54) MAGNETIC RESONANCE IMAGING SCANNER WITH COIL SERVING AS INDUCTOR OF POWER AMPLIFIER

(71) Applicant: Bilkent University, Ankara (TR)

(72) Inventors: Ergin Atalar, Ankara (TR); Redi Poni, Ankara (TR)

(73) Assignee: Bilkent University, Ankara (TR)

( * ) Notice: Subject to any disclaimer, the term of this patent is extended or adjusted under 35 U.S.C. 154(b) by 0 days.

(21) Appl. No.: 15/812,421

(22) Filed: Nov. 14, 2017

(65) Prior Publication Data

US 2018/0081003 A1 Mar. 22, 2018

Related U.S. Application Data

(63) Continuation of application No. PCT/KR2016/005150, filed on May 16, 2016.
(Continued)

(51) Int. Cl.
*G01R 33/36* (2006.01)
*A61B 5/055* (2006.01)
(Continued)

(52) U.S. Cl.
CPC .......... *G01R 33/3607* (2013.01); *A61B 5/055* (2013.01); *G01R 33/3614* (2013.01);
(Continued)

(58) Field of Classification Search
CPC ............ G01R 33/3607; G01R 33/3614; A61B 5/055; A61B 5/0816; A61B 5/0555; A61B 5/01; A61B 5/0402
(Continued)

(56) References Cited

U.S. PATENT DOCUMENTS 5,278,504 A 1/1994 Patrick
5,382,904 A 1/1995 Pissanetsky
(Continued)

FOREIGN PATENT DOCUMENTS

JP 2007167143 7/2007
JP 2008168132 7/2008
(Continued)

OTHER PUBLICATIONS

Gudino et al., "1.5T On-Coil Current-Mode Class-D (CMCD) Amplifier with Amplitude Modulation Feedback and voltage-Mode Class-D (VMCD) Preamplifier," Proc. Intl. Soc. Mag. Reson. Med. 18 (2010).
(Continued)

*Primary Examiner* — Farhana A Hoque
(74) *Attorney, Agent, or Firm* — Nelson Mullins Riley & Scarborough LLP; Thomas J. Engellenner; Reza Mollaaghababa

(57) ABSTRACT

According to an embodiment of the present disclosure, disclosed is an apparatus for generating a radio frequency (RF) pulse in a magnetic resonance imaging (MRI) scanner. The apparatus for generating a radio frequency (RF) pulse in a magnetic resonance imaging scanner includes: a control module controlling a power amplifier and a signal generator; the signal generator configured to generate a signal of a predetermined waveform based on control by the control module and supply the generated signal of the predetermined waveform to the power amplifier in electromagnetic connection therewith; a power amplifier amplifying the signal supplied from the signal generator based on the control by control module and outputting the amplified signal to a coil; and the coil serving as an inductor of the power amplifier and transferring the amplified signal to the object so that an object is excited.

19 Claims, 4 Drawing Sheets

Related U.S. Application Data

(60) Provisional application No. 62/161,741, filed on May 14, 2015.

(51) Int. Cl.
  *A61B 5/0402* (2006.01)
  *A61B 5/01* (2006.01)
  *A61B 5/08* (2006.01)

(52) U.S. Cl.
  CPC .............. *A61B 5/01* (2013.01); *A61B 5/0402* (2013.01); *A61B 5/0555* (2013.01); *A61B 5/0816* (2013.01)

(58) Field of Classification Search
  USPC .......................... 324/300–322; 600/407–435; 382/128–131
  See application file for complete search history.

(56) References Cited

U.S. PATENT DOCUMENTS

| | | | |
|---|---|---|---|
| 5,659,281 | A | 8/1997 | Pissanetsky |
| 6,016,439 | A | 1/2000 | Acker |
| 6,448,773 | B1 | 9/2002 | Zhang |
| 6,472,872 | B1 | 10/2002 | Jack, Jr. |
| 6,501,977 | B1 | 12/2002 | Kimmlingen |
| 6,563,315 | B1 | 5/2003 | Boskamp |
| 6,900,638 | B1 | 5/2005 | Yair |
| 7,202,734 | B1 * | 4/2007 | Raab .................... H03F 3/04 330/126 |
| 7,800,368 | B2 | 9/2010 | Vaughan |
| 8,125,225 | B2 | 2/2012 | Koretsky |
| 9,755,576 | B2 * | 9/2017 | Perreault ............... H03F 3/2176 |
| 9,923,518 | B2 * | 3/2018 | Perreault ............... H03F 3/2176 |
| 10,120,050 | B2 | 11/2018 | Feiweier |
| 2001/0024122 | A1 | 9/2001 | Mulder |
| 2007/0216409 | A1 | 9/2007 | Overweg |
| 2007/0279058 | A1 * | 12/2007 | Bulkes .............. G01R 33/34076 324/314 |
| 2008/0272784 | A1 | 11/2008 | Harvey |
| 2011/0254551 | A1 | 10/2011 | Leussler |
| 2014/0320132 | A1 | 10/2014 | Schmale |
| 2016/0181986 | A1 * | 6/2016 | Perreault ............... H03F 3/2176 330/251 |
| 2016/0181987 | A1 * | 6/2016 | Perreault ............... H03F 3/2176 330/251 |
| 2018/0011156 | A1 | 1/2018 | Atalar |
| 2018/0081003 | A1 * | 3/2018 | Atalar .................... A61B 5/055 |
| 2018/0120393 | A1 | 5/2018 | Atalar |
| 2018/0292502 | A1 | 10/2018 | Atalar |

FOREIGN PATENT DOCUMENTS

| | | |
|---|---|---|
| JP | 2008-264101 A | 11/2008 |
| JP | 2013-000591 A | 1/2013 |
| JP | 2014083445 | 5/2014 |
| KR | 10-0900862 B1 | 6/2009 |
| KR | 101503494 | 3/2015 |

OTHER PUBLICATIONS

International Search Report dated Aug. 22, 2016 in corresponding PCT Patent Application Serial No. PCT/KR2016/005150.
International Search Report dated Aug. 19, 2016 from PCT/KR2016/005160 (3 pages).
International Written Opinion dated Aug. 19, 2016 from PCT/KR2016/005160 (6 pages).
International Written Opinion dated Aug. 22, 2016 from PCT/KR2016/005150 (7 pages).

* cited by examiner

MAGNETIC RESONANCE IMAGING SCANNER WITH COIL SERVING AS INDUCTOR OF POWER AMPLIFIER

CROSS REFERENCE TO RELATED APPLICATIONS

This application is a continuation of International Patent Application No. PCT/KR2016/005150, filed on May 16, 2016, which claims the benefit of U.S. Provisional Patent Application Ser. No. 62/161,741, filed on May 14, 2015, each of which is hereby incorporated by reference in its entirety herein.

TECHNICAL FIELD

The present disclosure relates to a magnetic resonance imaging scanner, and more particularly, to an RF chain for generating an RF pulse.

BACKGROUND ART

Magnetic resonance imaging (MRI) provides an image based on information obtained through resonance after exposing an atomic nucleus to a magnetic field. The resonance of an atomic nucleus refers to a phenomenon in which when a specific high frequency radiation is incident in the atomic nucleus magnetized by an external magnetic field, the atomic nucleus in a low energy state is excited to a high energy state by absorbing high frequency energy. The atomic nuclei have different resonance frequencies depending on their type and the resonance is influenced by an intensity of an external magnetic field. There are innumerable atomic nuclei inside a human body and hydrogen atomic nuclei are generally used for magnetic resonance imaging.

In an MRI scanner, it is necessary to generate a radiofrequency (RF) pulse to be applied to an object during scanning. In general, a linear amplifier with kilowatt (kW) output power is used in the MRI scanner. In general, low efficiency of such a linear amplifier requires a cooling system, which increases a volume of the MRI scanner. In most cases, the amplifier is located outside a scanner room and away from a transmission coil, thereby additionally reducing efficiency and increasing overall cost of a system.

Therefore, there is a need for an MRI scanner that uses an amplifier having higher efficiency.

FIELD OF INVENTION

An object of the present disclosure is to provide a power amplifier having higher efficiency few use in an MRI scanner.

SUMMARY

According to an embodiment of the present disclosure for realizing the object, disclosed is an apparatus for generating a radio frequency (RF) pulse in a magnetic resonance imaging (MRI) scanner. The apparatus for generating a RF pulse in the magnetic resonance imaging scanner may include: a control module controlling a power amplifier and a signal generator; a signal generator configured to generate a signal of a predetermined waveform based on control by the control module and supply the generated signal of the predetermined waveform to the power amplifier in electromagnetic connection with the signal generator; the power amplifier amplifying the signal supplied from the signal generator based on the control by the control module and outputting the amplified signal to a coil; and the coil serving as an inductor of the power amplifier and transferring the amplified signal to the object so that the object is excited.

Alternatively, the power amplifier may include an input inductance component receiving power supplied from the signal generator, a switching transistor controlled by the control module, and one or more capacitors capable of storing electric charges.

Alternatively, the input inductance component may be configured by a transmission line including a coaxial cable, and the transmission line may have a length so that impedance of the transmission line is the same as the impedance when the input inductance component is configured by a choke inductor.

Alternatively, the coil may constitute the capacitor of the power amplifier and an LC leg, and the power amplifier may serve as a class E power amplifier.

Alternatively, load resistance added to the power amplifier may be a load added to the coil by the object and resistance of the coil.

Alternatively, the signal generator may supply a normal square waveform to the power amplifier.

Alternatively, the control module may be configured based on an FPGA, generate a binary bitstream, and turn on or off the switching transistor of the power amplifier.

Alternatively, a period of a bit of each of binary bitstream signals generated by the control module may be a half of a switching period of the power amplifier.

Alternatively, the control module may determine parameters of a circuit by pre-scanning the circuit of the power amplifier and supply the binary bitstream signal to the power amplifier based on the determined parameters.

Alternatively, the apparatus for generating an RF pulse in a magnetic resonance imaging scanner may further include a converter electrically connecting the coil and the control module so as to transfer the signal transferred to the coil to the control module, and the control module may control the power amplifier and the signal generator based on a feedback signal transferred through the converter.

Further, according to another embodiment of the present disclosure, disclosed is a magnetic resonance imaging scanner. The magnetic resonance imaging scanner may include an RF pulse generating apparatus, and the RF pulse generating apparatus may include a control module controlling a power amplifier and a signal generator, the signal generator configured to generate a signal of a predetermined waveform based on control by the control module and supply the generated signal of the predetermined waveform to the power amplifier in electromagnetic connection with signal generator, the power amplifier amplifying the signal supplied from the signal generator based on the control by the control module and outputting the amplified signal to a coil, and the coil serving as an inductor of the power amplifier and transferring the amplified signal to the object so that the object is excited.

According to the present disclosure, a power amplifier having higher efficiency can be applied to an MRI scanner.

DETAILED DESCRIPTION

Figure 1:
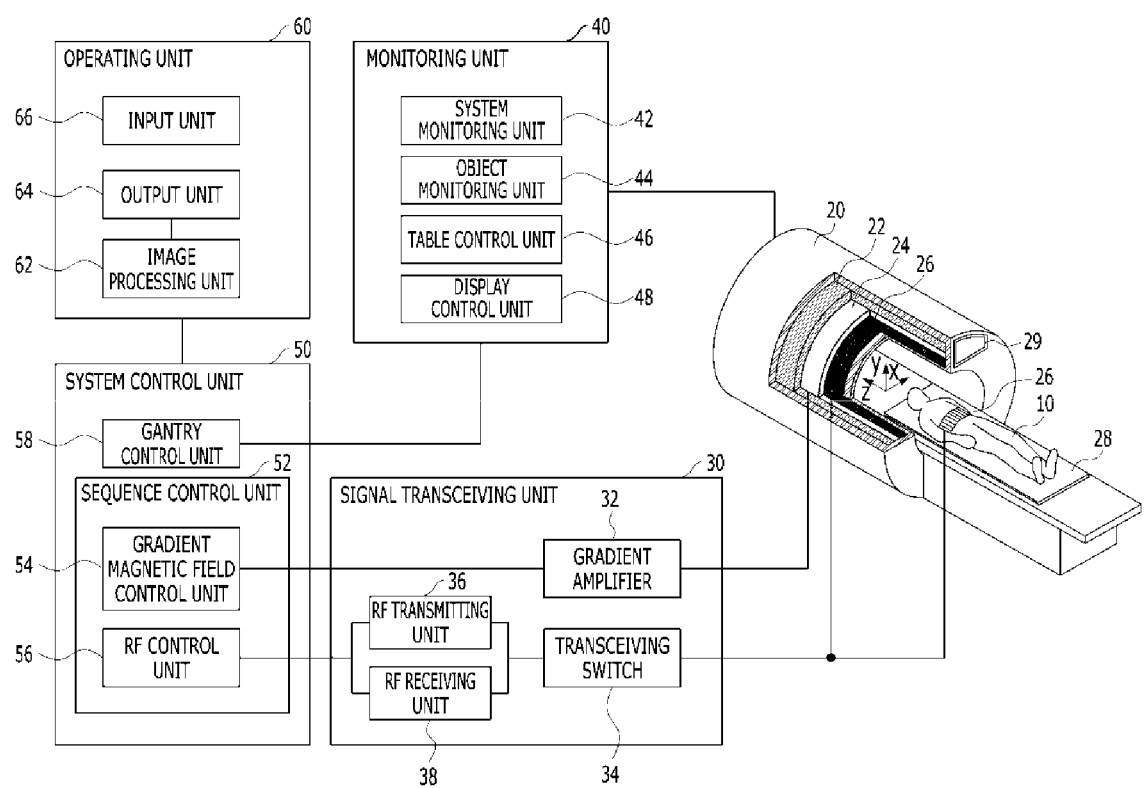
FIG. 1 is a block diagram illustrating a magnetic resonance imaging apparatus according to an embodiment of the present disclosure.

Various embodiments will be now described with reference to drawings and like reference numerals are used to refer to like elements throughout all drawings. In the present specification, various descriptions are presented to provide appreciation of the present disclosure. However, it is apparent that the embodiments can be executed without the specific description. In other examples, known structures and apparatuses are presented in a block diagram form in order to facilitate description of the embodiments.

Terms used in the present specification will be described in brief and the present disclosure will be described in detail. Terms used in the present disclosure adopt general terms which are currently widely used as possible by considering functions in the present disclosure, but the terms may be changed depending on an intention of those skilled in the art, a precedent, emergence of new technology, etc. Further, in a specific case, a term which an applicant arbitrarily selects is present and in this case, a meaning of the term will be disclosed in detail in a corresponding description part of the invention. Accordingly, a term used in the present disclosure should be defined based on not just a name of the term but a meaning of the term and contents throughout the present disclosure.

Further, throughout the specification, unless explicitly described to the contrary, the word "comprise" and variations such as "comprises" or "comprising", will be understood to imply the inclusion of stated elements but not the exclusion of any other elements. Further, the term "unit" used in the specification means software and/or hardware components such as FPGA or ASIC and the "unit" performs predetermined roles. However, the "unit" is not a meaning limited to software or hardware. The "unit" may be configured to reside on an addressable storage medium and may be configured to play back one or more processors.

Accordingly, as one example, the "unit" includes components such as software components, object oriented software components, class components, and task components, processes, functions, attributes, procedures, subroutines, segments of a program code, drivers, firmware, microcode, circuitry, data, databases, data structures, tables, arrays, and variables. Functions provided in the components and the "units" may be combined into a smaller number of components and "units" or further separated into additional components and "units."

An embodiment of the present disclosure will be described more fully hereinafter with reference to the accompanying drawings so as to be easily implemented by those skilled in the art. In addition, a part which is not related with the description is omitted in order to clearly describe the present disclosure in the drawings.

In the present specification, "image" may mean multi-dimensional data constituted by discrete image elements (e.g., pixels in a 2D image and voxels in a 3D image). For example, the image may include medical images of an object, which are acquired by X-ray, CT, MRI, ultrasonic waves, and other medical imaging systems, and the like. Further, in the present specification, the "object" may include a person or an animal, or a part of the person or the animal. For example, the object may include organs including liver, heart, uterus, brain, breast, abdomen, and the like or a blood vessel. Further, the "object" may include a phantom. The phantom means a material that has a density of a living thing and a volume that is very proximate to an effective atomic number and can include a spherical phantom that has a similar property to a human body.

Further, in the present specification, a "user" as a medical specialist may be a doctor, a nurse, a medical technologist, a medical imaging expert, or the like and a technician repairing a medical apparatus, but is not limited thereto.

Further, in the present specification, the term "magnetic resonance imaging (MRI)" means an image for an object obtained using a nuclear magnetic resonance principle.

In addition, in the present specification, the term "pulse sequence" means a series of signals repeatedly applied in the MRI apparatus. The pulse sequence may include a time parameter of an RF pulse, for example, a repetition time (TR) and a time to echo (TE).

Further, in the present specification, the term "TR" may mean the repetition time of the RF pulse. For example, the TR may mean a time between a transmission time of a first RF pulse and a transmission time of a second RF pulse.

Further, in the present specification, the term "pulse sequence schematic diagram" denotes an order in which the signals are applied in the MRI apparatus. For example, the pulse sequence schematic diagram may be a schematic diagram illustrating the RF pulse, a gradient magnetic field, a magnetic resonance signal, etc., with time.

Further, in the present specification, the term "spatial encoding" refers to obtaining spatial information along an axis (direction) of the gradient magnetic field by applying a linear gradient magnetic field that causes additional dephasing of a proton spindle in addition to dephasing of the proton spindle by an RF signal.

The MRI apparatus is an apparatus for acquiring an image of a single-layer portion of the object by expressing the intensity of a magnetic resonance (MR) signal for a radio frequency (RF) signal generated in a magnetic field of a specific intensity in contrast. For example, when the object is laid in a strong magnetic field and thereafter, the RF signal to resonate only a specific atomic nucleus (e.g., a hydrogen atomic nucleus, etc.) is irradiated to the object and stopped, the magnetic resonance signal is emitted from the specific atomic nucleus and the MRI apparatus may obtain an MR image by receiving the magnetic resonance signal. The magnetic resonance signal refers to the RF signal irradiated from the object. The magnitude of the magnetic resonance signal may be determined by the concentration of predetermined atoms (e.g., hydrogen, etc.) contained in the object, a relaxation time T1, a relaxation time T2, and a flow of a bloodstream.

The MRI apparatus includes features different from other imaging apparatuses. Unlike imaging apparatuses, such as CT, where acquisition of an image is dependent on a direction of detecting hardware, the MRI apparatus may acquire a two-dimensional image or a three-dimensional volumetric image directed to any point. Further, unlike CT, X-ray, PET, and SPECT, the MRI apparatus does not expose the object and an examinee to radiation, and may acquire an image having a high soft tissue contrast. Therefore, a neurological image, an intravascular image, a musculoskeletal image, and an oncologic image in which it is important to clearly describe an abnormal tissue may be obtained.

A three-dimensional volume of the object may include a three-dimensional shape of a person or animal, or part of the person or the animal. For example, the volume of the object may include the three-dimensional shape of organs including liver, heart, uterus, brain, breast, abdomen, and the like or a blood vessel, etc.

When the MRI apparatus intends to acquire information of the 3D volume of the object in a short time, it is possible to acquire a plurality of sheets of slice images in the direction of the slices constituting the 3D volume. When images of a plurality of slices are photographed, it is common to sequentially photograph the slice images as many as the slices, but taking the slice images sequentially may require a lot of time.

In a multi-slice scheme, when each slice image is acquired in a plurality of repetition time (TR) intervals, data for each slice is acquired in each TR interval in a cross direction to shorten a photographing time. For example, there is a dead time when the TR interval is much longer than an active time required for cross-section selection, phase encoding, and frequency encoding. In the multi-slice scheme, in order to obtain information on another cross section after obtaining information on one cross section in each TR interval, the dead time may be used.

In a simultaneous multi-slice (SMS) scheme, the plurality of slices are simultaneously excited to reduce a scan time to simultaneously acquire the magnetic resonance signals from the plurality of slices through a plurality of coils and a difference in coil sensitivity information which exists between the slices is used to separate the magnetic resonance signals for each slice. The coil sensitivity information may mean a sensitivity to receive different magnetic resonance signals depending on a location of each coil among the plurality of coils.

The simultaneous multi-slice scheme may correspond to parallel imaging, and the parallel imaging may include a sense scheme or a GRAPPA scheme.

FIG. 1 is a block diagram illustrating a magnetic resonance imaging apparatus according to an embodiment of the present disclosure.

Referring to FIG. 1, a magnetic resonance imaging apparatus may include a gantry 20, a signal transceiving unit 30, a monitoring unit 40, a device control unit 50, and an operating unit 60.

The gantry 20 may block electromagnetic waves generated by a main magnet 22, a gradient coil 24, an RF coil 26, etc. from being radiated to the outside. The gantry 20 may include a bore therein. An electromagnetic field and a gradient magnetic field may be formed in the bore and an RF signal may be irradiated from the bore toward an object 10.

The main magnet 22, the gradient coil 24, and the RF coil 26 may be disposed in a predetermined direction of the gantry 20. The predetermined direction may include a coaxial cylindrical direction, or the like. The object 10 may be positioned on a table 28 insertable into a cylinder along a horizontal axis of the cylinder.

The main magnet 22 may generate a static magnetic field for aligning a magnetic dipole moment of the atomic nuclei included in the object 10 in a predetermined direction.

As the magnetic field generated by the main magnet is stronger and more uniform, a relatively precise and accurate MR image with respect to the object 10 may be obtained.

The gradient coil 24 may include X, Y, and Z coils that generate a gradient magnetic field in mutually orthogonal X-, Y-, and Z-axis directions. The gradient coil 24 may provide positional information of each part of the object 10 by inducing resonance frequencies differently for each part of the object 10.

The RF coil 26 may irradiate RF signals to a patient and receive magnetic resonance signals emitted from the patient. For example, the RF coil 26 may transmit an RF signal having a frequency equal to a frequency of a processional motion toward the atomic nucleus which performs the processional motion to the patient and thereafter, stop transmission of the RF signal and receive the magnetic resonance signal emitted from the patient.

For example, the RF coil 26 may generate an electromagnetic signal, having a radio frequency corresponding to the type of atomic nucleus, for example, an RF signal, and apply the generated RF signal to the object 10 so as to transition a certain atomic nucleus from a low energy state to a high energy state. When the electromagnetic signal generated by the RF coil 26 is applied to the certain atomic nucleus, the certain atomic nucleus may transition from the low energy state to the high energy state. Thereafter, when the electromagnetic wave generated by the RF coil 26 is removed, the atomic nucleus to which the electromagnetic wave has been applied may emit electromagnetic waves having a Larmor frequency while transiting from the high energy state to the low energy state. In other words, when the application of the electromagnetic signal to the atomic nucleus is interrupted, while an energy level from high energy to low energy is changed in the atomic nucleus to which the electromagnetic wave is applied is changed, the electromagnetic wave having the Larmor frequency may be emitted. Here, the Larmor frequency may mean a frequency at which magnetic resonance is induced in the atomic nucleus.

The RF coil 26 may receive the electromagnetic signals irradiated from the atomic nuclei inside the object 10. The RF coil 26 may be implemented as one RF transceiving coil having both a function of generating the electromagnetic wave having the radio frequency corresponding to the type of the atomic nucleus and a function of receiving the electromagnetic waves irradiated from the atomic nucleus.

Further, the RF coil 26 may be implemented as each of a transmission RF coil having the function of generating the electromagnetic wave having the radio frequency corresponding to the type of atomic nucleus and a reception RF coil having the function of receiving the electromagnetic wave irradiated from the atomic nucleus.

Further, the RF coil 26 may be fixed to the gantry 20 and may be removable. The removable RF coil 26 may include RF coils for a portion of the object including a head RF coil, a thorax RF coil, a leg RF coil, a neck RF coil, a shoulder RF coil, a wrist RF coil, and an ankle RF coil.

Further, the RF coil 26 may communicate with an external device by a wired and/or wireless manner and may perform even dual tune communication according to a communication frequency band.

In addition, the RF coil 26 may include a birdcage coil, a surface coil, and a transverse electromagnetic coil (TEM coil) according to a structure of the coil.

In addition, the RF coil 26 may include a transmission-only coil, a reception-only coil, and a transmission/reception-combination coil according to a method of transceiving the RF signal.

Further, the RF coil 26 may include RF coils of various channels such as 16 channels, 32 channels, 72 channels, and 144 channels.

The gantry 20 may further include a display 29 positioned outside the gantry 20 and a display (not illustrated) positioned inside the gantry 20. Predetermined information may be provided to the user or the object via the displays positioned inside and outside of the gantry 20.

The signal transceiving unit 30 may control a gradient magnetic field formed in the gantry 20 according to a predetermined MR sequence and control transmission and reception of the RF signal and the magnetic resonance signal.

The signal transceiving unit 30 may include a gradient amplifier 32, a transceiving switch 34, an RF transmitting unit 36, and an RF receiving unit 38.

The gradient amplifier 32 may drive the gradient coil 24 included in the gantry 20 and supply a pulse signal for generating the gradient magnetic field to the gradient coil 24 under the control of the gradient magnetic field control unit 24.

The gradient magnetic field control unit 54 may control the pulse signal supplied from the gradient amplifier 32 to the gradient coil 24. By controlling the pulse signal supplied to the gradient coil 24, the gradient magnetic fields in X-axis, Y-axis, and Z-axis directions may be synthesized. The pulse signal may be implemented by current.

The RF transmitting unit 36 and the RF receiving unit 38 may drive the RF coil 26. The RF transmitting unit 36 may supply the RF pulse of the Larmor frequency to the RF coil 26 and the RF receiving unit 38 may receive the magnetic resonance signal received by the RF coil 26.

The transceiving switch 34 may adjust transmission/reception directions of the RF signal and the magnetic resonance signal. For example, the transceiving switch 34 may cause the RF signal to be irradiated to the object 10 through the RF coil 26 during a transmission mode and the magnetic resonance signal from the object 10 through the RF coil 26 to be received during a reception mode. The transceiving switch 34 may be controlled by a control signal from an RF control unit 56.

The monitoring unit 40 may monitor or control the gantry 20 or devices mounted on the gantry 20. The monitoring unit 40 may include a system monitoring unit 42, an object monitoring unit 44, a table control unit 46, and a display control unit 48.

The system monitoring unit 42 may monitor and control a state of the static magnetic field, the state of the gradient magnetic field, the state of the RF signal, the state of the RF coil, the state of a table, the state of a device for measuring body information of the object, a power supply state, the state of a heat exchanger, the state of a compressor, and the like.

The object monitoring unit 44 may monitor the state of the object 10. For example, the object monitoring unit 44 may include a camera for observing a motion or a position of the object 10, a respiration measuring unit for measuring respiration of the object 10, an ECG measurer for measuring an electrocardiogram of the object 10, or a body temperature measurer for measuring a body temperature of the object 10.

The table control unit 46 may control movement of the table 28 at which the object 10 is positioned. The table control unit 46 may control the movement of the table 28 according to sequence control of the sequence control unit 50. For example, in moving imaging of the object, the table control unit 46 may continuously or intermittently move the table 28 according to the sequence control by the sequence control unit 50 to thereby photograph the object in a field of view (FOV) larger than the FOV of the gantry.

The display control unit 48 may control the displays positioned outside and inside the gantry 20. For example, the display control unit 48 may control on/off of the displays positioned outside and inside the gantry 20 or a screen to be output to the display. Further, when a speaker is positioned inside or outside the gantry 20, the display control unit 48 may control the on/off of the speaker or a sound to be output through the speaker.

The system control unit 50 may include a sequence control unit 52 for controlling a sequence of signals formed in the gantry 20 and a gantry control unit 58 for controlling the devices mounted on the gantry 20.

The sequence control unit 52 may include the gradient magnetic field control unit 54 for controlling the gradient amplifier 32 and the RF control unit 56. The RF control unit 56 may control the RF transmitting unit 36, the RF receiving unit 38, and the transceiving switch 34.

The sequence control unit 52 may control the gradient amplifier 32, the RF transmitting unit 36, the RF receiving unit 38, and the transceiving switch 34 according to a pulse sequence received from the operating unit 60.

Here, the pulse sequence may include all information required for controlling the gradient amplifier 32, the RF transmitting unit 36, the RF receiving unit 38, and the transceiving switch 34 and may include, for example, information on the intensity, an application time, an application timing, and the like of the pulse signal applied to the gradient coil 24.

The operating unit 60 may instruct the pulse sequence information to the system control unit 50 and control an operation of the entire MRI apparatus.

The operating unit 60 may include an image processing unit 62 for processing the magnetic resonance signal received from the RF receiving unit 38, an output unit 64, and an input unit 66.

The image processing unit 62 processes the magnetic resonance signal received from the RF receiving unit 38 to generate magnetic resonance image data for the object 10.

The image processing unit 62 may perform various signal processing such as amplification, frequency conversion, phase detection, low frequency amplification, filtering, and the like on the magnetic resonance signal received by the RF receiving unit 38.

The image processing unit 62 arranges digital data in k-space data (also referred to as, for example, a Fourier space or a frequency space) of a memory and performs two-dimensional or three-dimensional Fourier transformation of the data to reconfigure the data into image data.

Further, the image processing unit 62 may perform synthesis processing or difference arithmetic processing of the image data as necessary.

The synthesis processing may include addition processing for a pixel, maximum value projection (MIP) processing, and the like. Further, the image processing unit 62 may store not only the reconfigured image data but also the image data subjected to the synthesis processing or the difference arithmetic processing in a memory (not illustrated) or an external server.

In addition, various signal processing applied to the magnetic resonance signal by the image processing unit 62 may be performed in parallel. For example, a plurality of magnetic resonance signals may be reconfigured into the image data by applying signal processing in parallel to the plurality of magnetic resonance signals received by a multi-channel RF coil.

The output unit 64 may output the image data or the reconfigured image data generated by the image processing unit 62 to the user. In addition, the output unit 64 may output information required for the user to operate the MRI apparatus, such as a UI (user interface), user information, or object information.

The output unit 64 may include a speaker, a printer, a CRT display, an LCD display, a PDP display, an OLED display, an FED display, an LED display, a VFD display, a DLP display, a PFD display, a 3D display, a transparent display, and the like and may include a variety of output devices within other scopes which are apparent to those skilled in the art.

The user may input object information, parameter information, a scan condition, the pulse sequence, information on image synthesis and calculation of difference, and the like using the input unit 66. The input unit 66 may include a keyboard, a mouse, a trackball, a voice recognition unit, a gesture recognition unit, a touch screen, and the like and may include various input devices within the other scopes which are apparent to those skilled in the art.

FIG. 1 illustrates the signal transceiving unit 30, the monitoring unit 40, the system control unit 50, and the operating unit 60 as separate objects, but those skilled in the art will be able to appreciate that functions performed by the signal transceiving unit 30, the monitoring unit 40, the system control unit 50, and the operating unit 60, respectively may be performed in different objects. For example, it is described above that the image processing unit 62 converts the magnetic resonance signal received by the RF receiving unit 38 into a digital signal, but the conversion into the digital signal may be autonomously performed by the RF receiving unit 38 or the RF coil 26.

The gantry 20, the RF coil 26, the signal transceiving unit 30, the monitoring unit 40, the system control unit 50, and the operating unit 60 may be connected to each other wirelessly or by wire and may further include a device (not illustrated) for synchronizing clocks with each other when the gantry 20, the RF coil 26, the signal transceiving unit 30, the monitoring unit 40, the system control unit 50, and the operating unit 60 are connected to each other wirelessly.

As communication among the gantry 20, the RF coil 26, the signal transceiving unit 30, the monitoring unit 40, the system control unit 50, and the operating unit 60, a high-speed digital interface such as low voltage differential signaling (LVDS), or the like, asynchronous serial communication such as universal asynchronous receiver transmitter (UART), false synchronization serial communication, a low-latency type network protocol such as a controller area network (CAN), or the like, an optical communication, or the like may be used and various communication methods may be used in the scope which is apparent to those skilled in the art.

Figure 2:
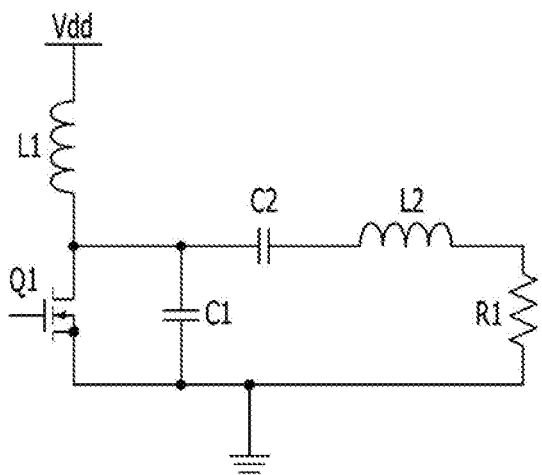
FIG. 2 is a diagram illustrating a class E amplifier.

FIG. 2 is a diagram illustrating a class E amplifier.

The MRI scanner according to one embodiment of the present disclosure may include a class E amplifier that shows higher efficiency than a conventional linear amplifier in order to reduce heat generation and prevent an increase in cost due to heat treatment. The class E amplifier may be a high efficiency switching power amplifier and may be used in high frequency situations where a switching time is similar to a duty time. A transistor of the class E amplifier may be connected to a load R1 through a serial LC circuit and to a power supply via an inductor L1. The power supply may be connected to a ground through a capacitor C1 to prevent leakage of the RF signal. When the transistor is ON, the class E amplifier may push power to the load through a serial LC (L2 and C2) circuit and some current may flow to the ground through a parallel LC circuit. In addition, the serial LC circuit may be pivoted to compensate the current of the parallel LC circuit. In this case, the current through the transistor may become 0 and the transistor may be switched to OFF. Energy may be charged in the inductor and the capacitor in the serial and parallel LC circuits and all circuits perform damped oscillation to allow the energy to be transferred to the load. The operation of the class E amplifier is just one example except for a DC component and the class E amplifier may serve as an amplifier with respect to various signals.

Figure 3:
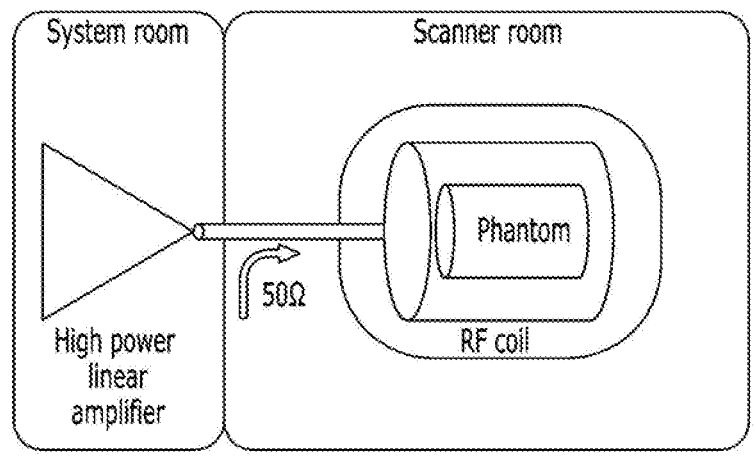
FIG. 3 is a diagram illustrating a system configuration of an MRI scanner in the related art.

FIG. 3 is a diagram illustrating a system configuration of an MRI scanner in the related art.

As the MRI scanner in the related art, the linear amplifier may be used, but since the linear amplifier shows low efficiency, the linear amplifier may require an additional cooling system. Accordingly, in the related art, the amplifier may exist outside a scanner room and may be electromagnetically coupled to the coil inside the scanner room via a long transmission line. Such a long transmission line causes loss by transmission line to reduce the efficiency of the entire system.

In addition, the MRI system using the linear amplifier in the related art requires the cooling system, and as a result, it is difficult to dispose the linear amplifier in the MRI scanner, which has a problem in terms of space utilization and a problem of reduction in efficiency due to the long transmission line.

Figure 4:
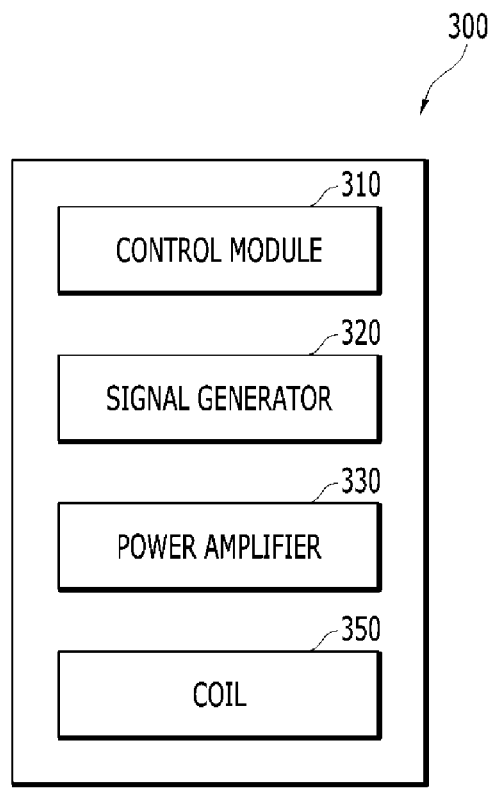
FIG. 4 is a block diagram of an RF pulse generating apparatus according to an embodiment of the present disclosure.

FIG. 4 is a block diagram of an RF pulse generating apparatus according to an embodiment of the present disclosure.

An apparatus 300 for generating the RF pulse according to an embodiment of the present disclosure may include a control module 310, a signal generator 320, a power amplifier 330, and a coil 350.

The signal generator 320 may generate a signal of a predetermined waveform and may be electromagnetically connected with the power amplifier 330 to supply the signal of the predetermined waveform generated by the power amplifier 330. The signal generator 320 may generate, for example, a normal square waveform signal, a bit stream signal, a DC signal, and supply the generated signals to the power amplifier 330. In addition, the signals may include the RF pulse.

The signal generator 320 may be an analog signal generator or a digital signal generator and may be controlled in an analog or digital manner.

The signal generator 320 may be digitally controlled by the control module. The signal generator may generate a signal to increase the efficiency of the amplifier by the control of the control module and transmit the generated signal to the power amplifier. An amplitude and a period of the output of the power amplifier 330 may be changed according to the type of signal of the signal generator 320 and further, may be changed according to the control signal of the control module 310.

The control module 310 is configured based on a field programmable gate array (FPGA) to control the signal generator 320 and the power amplifier 330 in the digital manner. The control module 310 generates a binary bit-stream signal composed of 0 and 1 to control a switching transistor 332 of the power amplifier 330. The control module 310 may turn on or off the switching transistor of the power amplifier 330 through the binary bitstream signal. The period of each bit of the binary bitstream signal generated by the control module 310 may be half of a switching period of the power amplifier 330.

The control module 310 may adjust the amplitude, frequency, waveform type, etc. of an output waveform of the power amplifier 330 by adjusting an on/off period of the switching transistor of the power amplifier 330.

In addition, since an input signal and an output signal in the class E power amplifier has linearity, the control module 310 may control the signal generator 320 to adjust the amplitude, frequency, waveform type, etc. of the output waveform of the power amplifier 330.

In addition, the control module 310 may control the power amplifier 330 and the signal generator 320 based on a feedback signal transmitted through the converter 360. The control module 310 may be fed back with the signal transferred to the coil from the converter to determine the parameters (R, L, C, etc.) of the circuit. Herein, a resistance component R among the circuit parameters may be a load added to the coil 350 by applying the RF pulse to the object. The control module 310 may determine the parameters of the circuit by pre-scanning the power amplifier circuit and supply the control signal to the power amplifier 330 and/or the signal generator 320 based on the determined parameters.

The control module 310 controls the switching transistor of the signal generator 320 or the power amplifier 330 to change the waveform, period, and amplitude of the RF pulse transferred to the coil.

The power amplifier 330 may amplify the signal supplied from the signal generator 320 based on the control of the control module 310 and output the amplified signal to the coil 350. In some embodiments, the power amplifier 330 may serve as a class E power amplifier.

Figure 6:
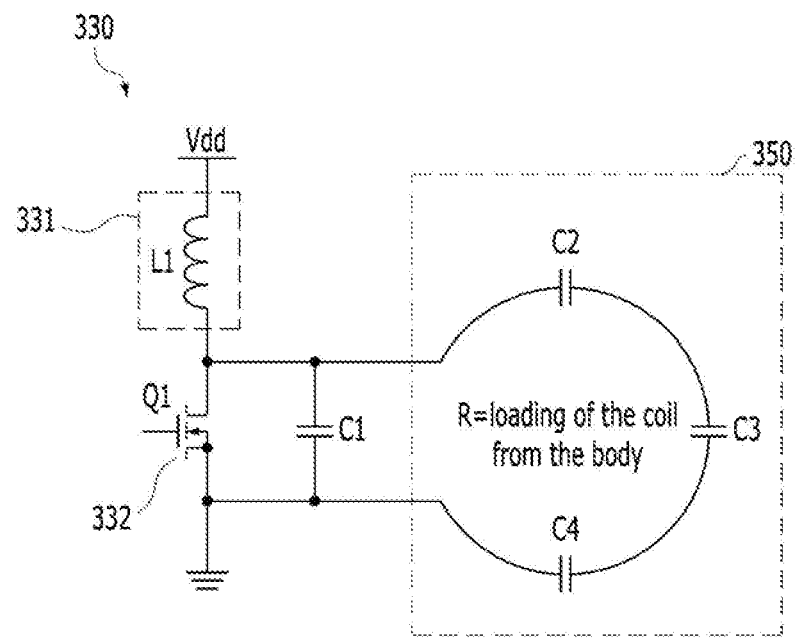
FIG. 6 is a diagram illustrating a power amplifier according to an embodiment of the present disclosure.

As illustrated in FIG. 6, the power amplifier 330 may include an input inductance component 331 for receiving the power supplied from the signal generator 320, a switching transistor 332 controlled by the control module 310, and one or more capacitors capable of storing electric charges. In addition, the coil 350 constitutes the capacitor of the power amplifier 330 and an LC leg so as to allow the power amplifier 330 to serve as the class E power amplifier.

As illustrated in FIG. 6, capacitors C2, C3, and C4 may be formed by capacitance corresponding to the capacitor C2 of FIG. 2 and lines connecting the capacitors C2, C3, and C4 may be configured in the form of the coil 350 and one or more capacitors and the coil 350 may thus constitute the LC leg. The load in the power amplifier 330 may be a load added to the coil by the object (e.g., a human body).

The switching transistor 332 of the power amplifier 330 may be digitally controlled by the control module 310. When the control module 310 is configured by a low voltage differential signals (LVDS) FPGA, the digital signal generated by the control module 310 may be converted into power capable of operating the switching transistor 332 through a driver 315. The switching transistor may be configured by, for example, BLF871 with a threshold voltage of 2.5 V, but the present disclosure is not limited thereto and an appropriate switching transistor element may be included within the scope of the present disclosure.

As the switching transistor 332 of the power amplifier 330 is controlled by the control module 310, the power amplifier 330 may perform energy storage and emission of the LC leg and serve as the class E power amplifier. The power amplifier 330 according to the embodiment of the present disclosure may reduce the number of all parts by configuring the coil 350 as a part of a load network and since the power amplifier 330 is directly connected to the coil, the output and the coil of the power amplifier need not be matched to 50Ω, thereby configuring a simpler circuit. Further, since a distance between the coil 350 and the power amplifier 330 decreases, the loss due to the longer transmission line may be reduced, thereby enhancing the efficiency of the entire system.

The input inductance component 331 of the power amplifier is configured by a transmission line including a coaxial cable and the transmission line may have a length such that impedance of the transmission line is equal to the impedance when the input inductance component is configured by a choke inductor. The input inductance component 331 is configured by the choke inductor is represented by a phasor domain, $Z=j2\pi fL$ and here, Z represents the impedance, f represents the frequency, and L represents inductance of the inductor. The impedance when the input inductance component 331 is configured by a coaxial cable having a length of l is $$Z = jZ_0 \tan\left(\frac{2\pi fl}{c}\right)$$

and here, Z represents the impedance, $Z_o$ represents a characteristic impedance of the coaxial cable, l represents the length of the transmission line, and c represents a velocity of the electromagnetic wave in the transmission line. The length l of the coaxial cable may be determined to have the same impedance Z in two cases. Here, the length l of the transmission line may be determined as $$l = \frac{c}{2\pi f}\tan^{-1}\left(\frac{2\pi fL}{Z_0}\right).$$

When the input inductance component 331 of the power amplifier is configured through the transmission line, a power amplifier having a shorter transmission line may be configured, and as a result, the volume of the power amplifier 330 is reduced so as to allow disposing the power amplifier 330 inside the scanning room. Further, the input inductance component 331 according to the embodiment of the present disclosure may be configured by a strip line or a microstrip on a printed circuit board.

The coil 350 may generate the electromagnetic signal, having the radio frequency corresponding to the type of atomic nucleus, for example, the RF signal and apply the generated RF signal to the object 10 so as to transition a certain atomic nucleus from the low energy state to the high energy state. Further, the coil 350 may receive the electromagnetic signals irradiated from the atomic nuclei inside the object 10. The coil 350 may correspond to the RF coil 26.

The generation of the RF pulse according to the embodiment of the present disclosure may operate in at least three modes.

First operating mode: Mode in which the switching transistor 332 is switched to a 50% duty cycle of a normal square waveform and a signal having a variable envelope in the signal generator is supplied to the power amplifier 330 through modulation of the signal generator 320 to allow the power amplifier 330 to amplify and output the supplied signal.

Second operating mode: Mode in which the signal generator 320 supplies a signal having a predetermined envelope and controls the output of the power amplifier 330 by generating the bitstream signal to control the switching transistor 332 by the control module 310 to generate the RF pulse.

Third operating mode: Mode to adjust both the envelope modulation of the signal generator and the duty cycle of the switching transistor signal by combining the first and second operating modes.

In the first operating mode, the RF pulse generating apparatus 300 may control each of on and off of the switching transistor 332 to occupy a half weight through a signal configured by 101010 . . . from the control module 310 and output a desired RF pulse through adjusting the envelope, amplitude, frequency, etc. of the waveform supplied from the signal generator 320.

In the second operating mode, the RF pulse generating apparatus 300 allows the signal generator 320 to supply the signal having the predetermined envelope to the power amplifier 330 and controls the weight of each of the on and off cycles of the switching transistor 332 through the control module 310 (that is, the signal supplied by the control module 310 is not 101010 . . . and the weights of 1 and 0 may not be equal to each other like 1101001, etc.) to output the desired RF pulse.

In the third operating mode, the RF pulse generating apparatus 300 adjusts the envelope, amplitude, frequency, etc. of the waveform supplied from the signal generator 320 to the power amplifier 330 and controls the weight of each of the on and off cycles of the switching transistor 332 through the control module 310 to output the desired RF pulse.

Figure 5:
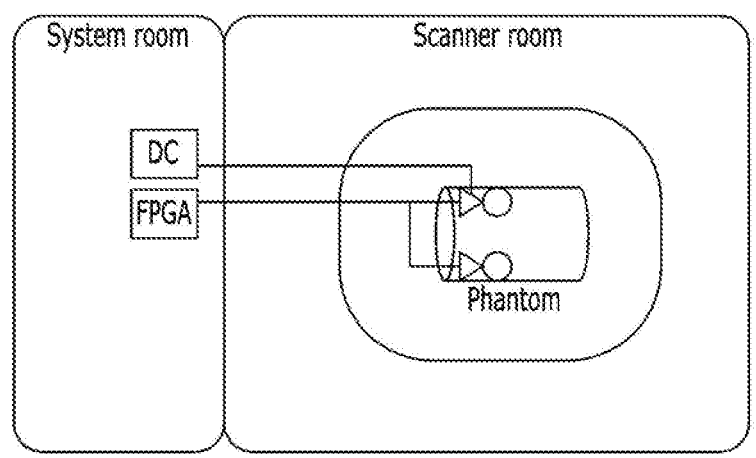
FIG. 5 is a diagram illustrating a system configuration of an MRI scanner according to an embodiment of the present disclosure.

FIG. 5 is a diagram illustrating a system configuration of an MRI scanner according to an embodiment of the present disclosure.

The MRI scanner according to the embodiment of the present disclosure may include the class E power amplifier, which is a type of non-linear amplifier. The power amplifier 330 according to the embodiment of the present disclosure has high efficiency and the need for the cooling system may be reduced as compared with a system configuration in the related art. In addition, the MRI scanner according to the embodiment of the present disclosure may constitute a multi-channel RF transmitter through a plurality of power amplifiers and a plurality of coils. The coil 350 according to the embodiment of the present disclosure serves as the load network of the power amplifier 330 so that the coil 350 and the power amplifier 330 may be disposed close to each other. Further, therefore, the overall volume of the coil 350 and the power amplifier 330 is reduced to allow the coil 350 and the power amplifier 330 to be disposed inside the MRI scanner inside the scanning room. The control module 310 for controlling the power amplifier 330 and the signal generator 320 capable of supplying the signal to the power amplifier 330 may be positioned in a system room which is a different space from the power amplifier 330 or positioned together with the power amplifier 330. FIG. 5 illustrates an exemplary configuration and the present disclosure is not limited thereto and the signal generator 320 and the control module 310 may also be positioned in the scanning room.

Figure 7:
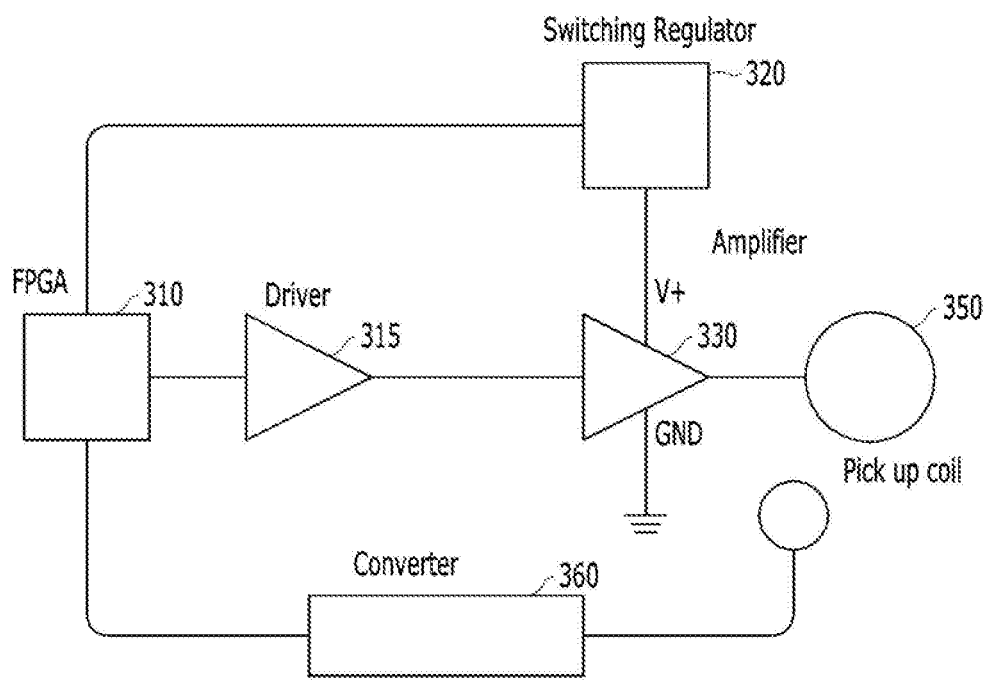
FIG. 7 is a block circuit diagram of the RF pulse generating apparatus according to an embodiment of the present disclosure.

FIG. 7 is a block circuit diagram of the RF pulse generating apparatus according to an embodiment of the present disclosure.

The RF pulse generating apparatus 300 according to the embodiment of the present disclosure may include the control module 310, the driver 315, the signal generator 320, the power amplifier 330, the coil 350, and the converter 360. FIG. 7 illustrates a block for simplifying the respective components of the circuit.

The control module 310 may control the power amplifier 330 and the signal generator 320. The control module 310 is configured based on the FPGA and generates the bitstream to control the switching transistor 332 of the power amplifier. Further, the control module 310 may control the switching transistor 332 of the power amplifier by generating an optical signal or a single ended signal.

The driver 315 may convert the digital signal generated by the control module 310 into voltage that allows the switching transistor 332 to operate. When the control module 310 is configured by the low voltage differential signals (LVDS) FPGA, the voltage of the signal generated by the control module 310 may be lower than 0 to 5 V which is driving voltage of the switching transistor 332. The driver 315 may convert the digital signal of the control module 310 into the driving voltage of the switching transistor 332 and transfer the converted driving voltage to the power amplifier 330. Further, depending on the driving voltage of the switching transistor 332, the driver 315 may not be required. When the output of the control module 310 is sufficient to drive the switching transistor 332, the driver 315 may not be required.

The signal generator 320 may generate, for example, a normal square waveform signal, a bit stream signal, a DC signal, and the like and supply the generated signals to the power amplifier 330. In addition, the signals may include the RF pulse. The signal generator 320 may generate a pulse shape (e.g., sinc, rect, etc.) through amplitude modulation. The signal generator 320 may be implemented, for example, through a half-bridge switching converter and a low pass filter.

The converter 360 may constitute the feedback circuit by connecting the coil 350 and the control module 310. The converter 360 may extract the envelope of the signal from the coil 350 and convert the extracted envelop into the digital signal and transmit the digital signal to the control module 310.

The RF pulse that may be output through the coil 350 of the present disclosure may be generated in the signal generator 320 and amplified and output. Further, the signal generator 320 may supply DC voltage to the power amplifier 330 and the control module 310 may allow the power amplifier 330 to output the RF pulse by controlling the switching transistor 332 of the power amplifier 330. The control module 310 may supply the power amplifier with the control signal for controlling the switching timing of the power amplifier 330. Further, the signal generator 320 may supply a desired waveform to the power amplifier 330 under the control module 310 so that the RF pulse may be output from the power amplifier 330.

It will be appreciated by those skilled in the art that information and signals may be expressed by using various different predetermined technologies and techniques. For example, data, instructions, commands, information, signals, bits, symbols, and chips which may be referred in the above description may be expressed by voltages, currents, electromagnetic waves, magnetic fields or particles, optical fields or particles, or predetermined combinations thereof.

It may be appreciated by those skilled in the art that various exemplary logical blocks, modules, processors, means, circuits, and algorithm steps described in association with the embodiments disclosed herein may be implemented by electronic hardware, various types of programs or design codes (for easy description, herein, designated as "software"), or a combination of all of them. In order to clearly describe the intercompatibility of the hardware and the software, various exemplary components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be analyzed that the implementation determination departs from the scope of the present disclosure.

Further, various embodiments presented herein may be implemented as manufactured articles using a method, an apparatus, or a standard programming and/or engineering technique. The term "manufactured article" includes a computer program, a carrier, or a medium which is accessible by a predetermined computer-readable device. For example, a computer-readable medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information. The term "machine-readable media" includes a wireless channel and various other media that can store, posses, and/or transfer command(s) and/or data, but are not limited thereto.

It will be appreciated that a specific order or a hierarchical structure of steps in the presented processes is one example of exemplary accesses. It will be appreciated that the specific order or the hierarchical structure of the steps in the processes within the scope of the present disclosure may be rearranged based on design priorities. Appended method claims provide elements of various steps in a sample order, but it does not mean that the method claims are limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be analyzed within the widest range which is consistent with the principles and new features presented herein.

Related contents in the best mode for carrying out the present disclosure are described as above.

The present disclosure may be used in a magnetic resonance imaging apparatus.

Those having ordinary skill in the art will appreciate that various changes can be made to the above embodiments without departing from the scope of the invention.

What is claimed is:

1. An apparatus for generating a radio frequency (RF) pulse in a magnetic resonance imaging (MRI) scanner, the apparatus comprising:
a plurality of control modules controlling a plurality of Class E power amplifiers,
wherein based on control by each control module of the plurality of control modules each amplifier of the plurality of amplifiers is configured to receive a predetermined supply signal and amplify the signal, such that the signal on each amplifier is independent; and
a plurality of coils, each amplifier being electrically connected to a coil of the plurality of coils and each amplifier outputting the amplified signal to
the electrically connected coil thereto,
wherein each output amplified signal is configured such that its waveform, period, and/or amplitude to the coil is independently controlled, and
wherein each coil of the plurality of coils serves as an inductor for its electrically connected power amplifier and further transfers the amplified signal to the object so that the object is excited.

2. The apparatus of claim 1, wherein each power amplifier comprises:
a choke inductance component receiving power supplied from a signal generator,
a switching transistor controlled by each control module, and
one or more capacitors capable of storing electric charges.

3. The apparatus of claim 2, wherein the signal generator supplies a normal square waveform to at least one of the power amplifiers.

4. The apparatus of claim 2, wherein each control module is configured based on an FPGA, generates a binary bitstream, and turns on or off the switching transistor of each power amplifier.

5. The apparatus of claim 4, wherein a period of a bit of each of binary bitstream signals generated by each control module is a half of a switching period of each power amplifier.

6. The apparatus of claim 4, wherein each control module determines parameters of a circuit by pre-scanning the circuit of each power amplifier and supplies the binary bitstream signal to each power amplifier based on the determined parameters.

7. The apparatus of claim 2, further comprising a converter electrically connecting each coil and control module so as to transfer the signal, wherein each control module controls each power amplifier and signal generator based on a feedback signal transferred through the converter.

8. The magnetic resonance imaging scanner of claim 2, wherein the choke inductance component is configured by a choke inductor.

9. The magnetic resonance imaging scanner of claim 8, wherein the transmission line is selected from the group consisting of a coaxial cable, a microstrip, and a strip line.

10. The apparatus of claim 2, wherein the apparatus is characterized by an impedance for the choke inductance component is such that the impedance is the same for both a length of transmission line and for a choke inductor.

11. The apparatus of claim 2, wherein the choke inductance component is configured by a transmission line.

12. The apparatus of claim 1, wherein each power amplifier is characterized by a sum of coil resistance and object resistance.

13. The apparatus of claim 1, wherein the coil is a capacitor and an LC leg.

14. A magnetic resonance imaging scanner, comprising:
an RF pulse generating apparatus,
wherein the RF pulse generating apparatus comprises:
a plurality of control modules controlling a plurality of Class E power amplifiers,
wherein based on control by each control module of the plurality of control modules each amplifier of the plurality of amplifiers is configured to receive a predetermined supply signal and amplify the signal, such that the signal on each amplifier is independent; and
a plurality of coils, each amplifier being electrically connected to a coil of the plurality of coils and each amplifier outputting the amplified signal to
the electrically connected coil thereto,
wherein each output amplified signal is configured such that its waveform, period, and/or amplitude to the coil is independently controlled, and
wherein each coil of the plurality of coils serves as an inductor for its electrically connected power amplifier and further transfers the amplified signal to the object so that the object is excited.

15. The magnetic resonance imaging scanner of claim 14, wherein each power amplifier comprises:
   a choke inductance component receiving power supplied from a signal generator,
   a switching transistor controlled by the control module, and
   one or more capacitors capable of storing electric charges.

16. The magnetic resonance imaging scanner of claim 15, wherein the choke inductance component is configured by a transmission line.

17. The magnetic resonance imaging scanner of claim 15, wherein the choke inductance component is configured by a choke inductor.

18. The magnetic resonance imaging scanner of claim 17, wherein the transmission line is selected from the group consisting of a coaxial cable, a microstrip, and a strip line.

19. The magnetic resonance imaging scanner of claim 15, wherein the apparatus is characterized by an impedance for the choke inductance component is such that the impedance is the same for both a length of the transmission line and for a choke inductor.

\* \* \* \* \*